United States Patent
Shtakelberg et al.

(10) Patent No.: US 8,610,444 B2
(45) Date of Patent: Dec. 17, 2013

(54) METHOD AND SYSTEM FOR ANALYZING A CHEMICALLY-ACTIVE MATERIAL

(75) Inventors: David Shtakelberg, Modiln (IL); Boris Vilge, Lapid (IL); Shimon Boyko, Har-Adar (IL)

(73) Assignee: Concretec Ltd., Jerusalem (IL)

( * ) Notice: Subject to any disclaimer, the term of this patent is extended or adjusted under 35 U.S.C. 154(b) by 894 days.

(21) Appl. No.: 12/759,730

(22) Filed: Apr. 14, 2010

(65) Prior Publication Data
US 2011/0254573 A1  Oct. 20, 2011

(51) Int. Cl.
*G01R 27/08*  (2006.01)
(52) U.S. Cl.
USPC .............................. 324/693; 324/300; 73/803
(58) Field of Classification Search
USPC .................................... 324/300, 693; 73/803
See application file for complete search history.

(56) References Cited

U.S. PATENT DOCUMENTS 5,672,968 A * 9/1997 Miller et al. ................... 324/300
6,819,121 B1 * 11/2004 Hager, III et al. ............. 324/664

OTHER PUBLICATIONS

Request for Formal Expertise Dated Sep. 2, 2010 From the Rospatent, Federal Government Institution, 'Federal Institute of Industrial Property of the Federal Service for Intellectual Property, Patents and Trademarks' (FGI FIIP) Re. Application No. 2010114836 Including Associate's Letter in English.
Response Dated Jun. 26, 2011 to the Request for Formal Expertise of Sep. 2, 2010 From the Rospatent, Federal Government Institution, 'Federal Institute of Industrial Property of the Federal Service for Intellectual Property, Patents and Trademarks' (FGI FIIP) Re. Application No. 2010114836.

* cited by examiner

*Primary Examiner* — Arleen M Vazquez

(57) ABSTRACT

A method of determining setting period of a chemically-active material is disclosed. The method comprises: continuously measuring an electrical property such as of the material to provide a time-dependence of the property, and using the time-dependence for defining a setting-start time and a setting-finish time. The setting-start time is defined as a time of onset of a fastest rise of the resistivity and the setting-finish time is defined as a time of local maximum of the resistivity.

26 Claims, 13 Drawing Sheets

METHOD AND SYSTEM FOR ANALYZING A CHEMICALLY-ACTIVE MATERIAL

FIELD AND BACKGROUND OF THE INVENTION

The present invention, in some embodiments thereof, relates to material analysis and, more particularly, but not exclusively, to the analysis of chemically-active material that undergoes a curing process when hardening, such as, but not limited to, cementitious material, e.g., concrete.

A chemically-active material often needs to be analyzed so as to determine the structural properties, e.g., strength and other physical-mechanical properties of the final cured product, such as its potential for shrinkage. The final strength of a chemically-active capillary-porous material is determined by the properties of the initial raw materials, mixing and compacting conditions, and specific composition such as mineral binder-to-aggregate ratio, water-to-cement ratio, water-to-aggregate ratio and the like [Neville A. M., "Properties of concrete," Longman Scientific & Technical, 1981].

The hardening process of a chemically-active material can be considered as a series of consecutive transitions between different states of the material.

Initially, the material is a compaction structure who's physical and mechanical properties are determined mainly by compressive actions of capillary pressure on "water-air" boundaries. This state is characterized by an intensive development of the chemical reactions, such as hydration and hydrolysis and formation of gel (the term gel has been introduced into the scientific practice in conjunction to cementitious materials by T. Powers in an article entitled "The non-evaporable water content of hardened Portland cement pastes," published in ASTM Bulletin, 1949, No. 158, and was further used by A. Neville in an article entitled "Properties of concrete," published by Longman Scientific & Technical, 1961).

In a second state following the initial state, the material develops a coagulation structure, which is a capillary-porous colloidal body having chemically-active water-silicate dispersions.

In a third state the material develops a colloidal-crystalline structure, which is a quasi-solid capillary porous body. In this state the gel begins to age and crystalline structures are formed.

In a fourth state, the crystalline structures condensate, and the material has a solid capillary-porous body whose conditions are determined by the laws governing the interaction of particles and particle aggregates in the solid phase.

At any given state, the chemically-active material has a poly-dispersed structure of a moist capillary-porous body. The liquid phase of the material is therefore an informative component indicative of the porosity of the material and therefore of its strength. Water (both in a liquid and gaseous form) is always in a state of thermodynamic equilibrium with the porous solid phase with which it interacts. Thus, the properties of water are changing in strict accordance with structure formation and consequently with the strength growth of the hardening material. To this end, see, for example, Shtakelberg D. I. and Sithcov M. M., "Self-organization in disperse systems," Riga, "Zinatne" Press, 1990; and Shtakelberg D. I., "Thermodynamics of water-silicate disperse materials structure-formation," Riga, Zinatne, 1984; and Neville M. "Properties of concrete," Longman Scientific & Technical. NT., 1988.

The duration of the above hardening process is typically rather long. For example, in cementitious materials typical duration of hardening is of order of one month, at which time the cement passes through all the above states and becomes a solid structure of a given compressive strength.

Due to the long duration of the hardening process, prior to reaching the final strength, the chemically-active material undergoes many complicated physical and chemical processes, which can essentially affect its physical properties. It is recognized that any change, deviation and non-observance of the technological regulations during preparation of the chemically-active material, such as ready-mixed or pre-cast concrete, may irreversibly reduce the properties (e.g., strength) of the final product. Reasons for poor final product quality include unexpected replacement of material suppliers, improper operation of the equipment or failure thereof and the like.

Hardening and strengthening of chemically-active material is initiated immediately once the compaction for a particular application is completed. However, many additional processes, affecting the final quality can takes place. For example, in case of concrete, the transportation of the mix from the manufacturing plant to the building site typically occurs between the preparation of the mix and the compaction thereof. Although during transportation the concrete mix is in a continuous motion inside a rotating drum so as to prevent setting or hardening, it is known that the final properties of cementitious products made after a prolonged transportation of the mix are different from the properties of the same products when made of a freshly prepared mix.

Prolonged transportation of the mix naturally extends the period in which chemical reactions such as hydration and hydrolysis occur. Thus, upon arrival to the construction site different transport durations result in different initial states for the hardening and strengthening processes evolve.

Other factors which are known to alter the hardening process include, chemical additives of various functional purposes, temperature conditions during hardening, curing conditions of the freshly formed concrete, non-homogeneity of the mix, complexity and duration of the manufacturing process and the like.

Traditionally, the hardening process of concerted is monitored mechanically, via one or more techniques, such as slump test, VeBe consistency test, setting time test, compressive strength test and the like.

In the slump test, a cone (called slump cone) is placed on a base and filled with concrete. The cone is lifted up, leaving a heap of concrete that slumps. The slump cone is placed on the base to act as a reference and the difference in level between its top and the top of the concrete is measured. The slump test is typically employed for fresh concretes during the first 3 hours from preparation of the concrete mixture. Fast slump (also referred to in the literature as "high" slump) is observed when the amount of physically bound water in the concrete is relatively high, and slow slump (also referred to in the literature as "low" slump) is observed when the amount of physically bound water in the concrete is relatively low.

In the VeBe (also known as VB) consistency test the work needed to compact the concrete is measured. A slump cone of concrete is placed on a table and the cone is lifted as in the slump test. The table is vibrated at a standard rate. The time taken for the concrete to be compacted is measured. Vebe times range from 1 second for runny concrete to more than 12 seconds for stiff concrete. The VeBe test is typically employed during the period of 3-10 hours from preparation of the concrete mixture.

In the setting time test, the time of setting of concrete is estimated by means of penetration resistance measurements on mortar sieved from the concrete mixture. The penetrating device is shaped as a needle or wedge and is known as a Proctor needle. The Proctor needle is typically employed during the period of 10-24 hours from preparation of the concrete mixture.

The compressive strength test is typically performed post-curing. Concrete specimen is placed in a pressing machine and subjected to a gradually increasing compressive pressure so as to determine the failure load. The compressive strength is defined as ratio between the failure load and the cross-sectional area resisting the load. Also known is the pull-off test wherein an axial pull-off force is applied to a steel plate fixed to the concrete surface; and the pin penetration test wherein a smooth pin is driven into the concrete and the depth of penetration and/or pull out strength are measured.

Li et al. ["Determination of Concrete Setting Time Using Electrical Resistivity Measurement," Journal of Materials in Civil Engineering, Vol. 19, No. 5, 423-427 (2007)] disclose a technique for determining concrete setting time using electrical resistivity measurement. Two critical points are identified on the resistivity curve and the setting times are estimated as linear functions of the abscissa values of the critical points.

Other techniques are disclosed in International Publication Nos. WO2001/065282, WO2005/047891 and WO2005/124339, and U.S. Pat. Nos. 6,396,265, 7,181,978, and 7,225,682, the contents of which are hereby incorporated by reference.

SUMMARY OF THE INVENTION

According to one aspect of the present invention there is provided a method of determining setting period of a chemically-active material. The method comprises: continuously measuring an electrical property of the material to provide a time-dependence of the property, the property being a resistivity or a proxy thereof; using the time-dependence for defining a setting-start time and a setting-finish time, wherein the setting-start time is defined as a time of onset of a fastest rise of the resistivity and the setting-finish time is defined as a time of local maximum of the resistivity; thereby determining the setting period of the material.

According to some embodiments of the invention the method further comprises using the time-dependence for identifying transition between a workable state of the material and a non-workable state of the material.

According to some embodiments of the invention the method further comprises using the time-dependence for identifying transition between a first workable state of the material and a second workable state of the material, the transition being equivalent to an abrupt slowing of slump that would have been observed had the material been subjected to a slump test.

According to some embodiments of the invention the method further comprises using the time-dependence for identifying transition between a gel state of the material and a capillary-porous colloidal state of the material.

According to some embodiments of the invention the method further comprises using the time-dependence for identifying transition between a capillary-porous colloidal state of the material and a colloidal-crystalline state of the material.

According to some embodiments of the invention the method further comprises using the time-dependence for identifying transition between a discontinuous crystalline state of the material and a continuous crystalline state of the material.

According to some embodiments of the invention the method further comprises using the time-dependence for determining a compressive strength of the material.

According to another aspect of the present invention there is provided a system for determining setting period of a chemically-active material. The system comprises a measuring unit, for continuously measuring an electrical property of the material to provide a time-dependence of the property, the property being a resistivity or a proxy thereof; and a processing unit, for defining, based on the time-dependence, a setting-start time and a setting-finish time, wherein the setting-start time is defined as a time of onset of a fastest rise of the resistivity and the setting-finish time is defined as a time of local maximum of the resistivity.

According to some embodiments of the invention the processing unit is configured for identifying transition between a workable state of the material and a non-workable state of the material, based on the time-dependence.

According to some embodiments of the invention the transition between the workable and the non-workable states is defined as a time of local minimum of the resistivity.

According to some embodiments of the invention the transition between the workable and the non-workable states is identified on a linear scale of the time-dependence.

According to some embodiments of the invention the local minimum is identified using a moving time window having a width of about 2 hours.

According to some embodiments of the invention the processing unit is configured for identifying transition between a first workable state of the material and a second workable state of the material, based on the time-dependence, the transition being equivalent to an abrupt slowing of slump that would have been observed had the material been subjected to a slump test.

According to some embodiments of the invention the transition between the first and the second workable states is defined as a time corresponding to a point of inflection of the resistivity.

According to some embodiments of the invention the transition between the first and the second workable states is identified on a linear scale of the time-dependence.

According to some embodiments of the invention the point of inflection is identified using a moving time window having a width of about 2 hours.

According to some embodiments of the invention the processing unit is configured for identifying transition between a gel state of the material and a capillary-porous colloidal state of the material, based on the time-dependence.

According to some embodiments of the invention the processing unit is configured for identifying transition between a capillary-porous colloidal state of the material and a colloidal-crystalline state of the material, based on the time-dependence.

According to some embodiments of the invention the processing unit is configured for identifying transition between a discontinuous crystalline state of the material and a continuous crystalline state of the material, based on the time-dependence.

According to some embodiments of the invention the processing unit is configured for determining a compressive strength of the material, based on the time-dependence.

According to some embodiments of the invention each of the setting-start and the setting-finish times is identified on a linear scale of the time-dependence.

According to some embodiments of the invention each of the onset of the fastest rise of the resistivity and the local maximum of the resistivity are identified using a moving time window having a width of about 2 hours.

According to some embodiments of the invention the electrical property is measured by direct contact with the material.

According to some embodiments of the invention the electrical property is measured in a constant volume.

According to some embodiments of the invention the electrical property is measured by generating an electric field between a first electrode and a second electrode along a sufficiently long contour within the material.

According to some embodiments of the invention the contour has a length which is at least two times the distance between the electrodes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
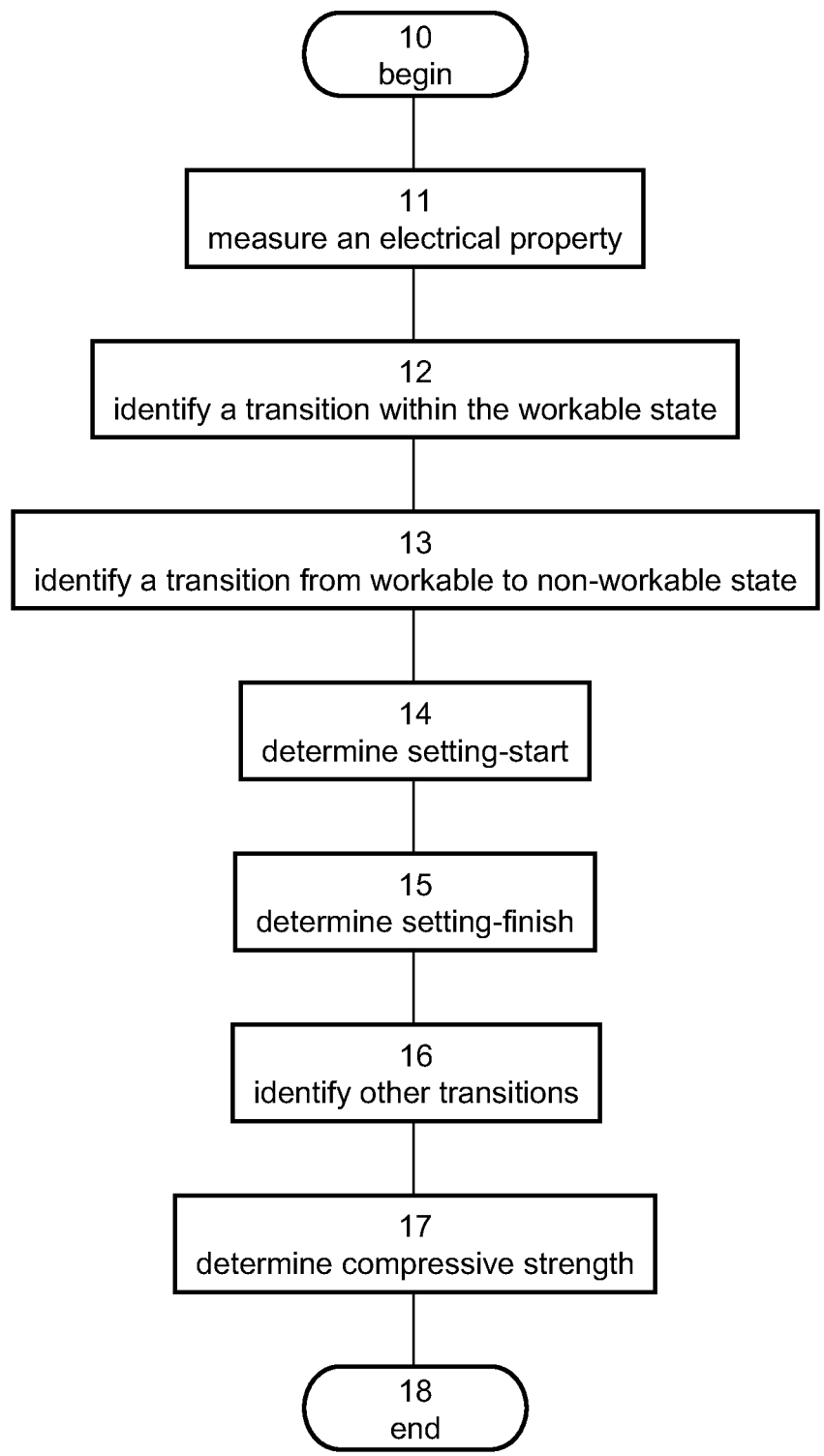
FIG. 1 is a flowchart diagram of a method suitable for determining a setting period of a chemically-active material, according to various exemplary embodiments of the present invention.

The present invention, in some embodiments thereof, relates to material analysis and, more particularly, but not exclusively, to the analysis of chemically-active material that undergoes a curing process when hardening, such as, but not limited to, cementitious material, e.g., concrete.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As used herein, chemically-active material is a material that undergoes a curing process when hardening. Representative examples of chemically-active materials analyzable by the present embodiments, include cementitious materials, e.g., concrete, mortar, as well as non-cementitious materials, e.g., gypsum slurry, clay slurry and ash slurry. Other chemically-active materials analyzable by the present embodiments are curable organic pastes, such as, but not limited to, epoxy-based pastes.

Since concrete and similar cementitious materials are widely used due to their high versatility and low-cost, the embodiments below are described with a particular emphasis to concrete. However, it is to be understood that more detailed reference to concrete is not to be interpreted as limiting the scope of the invention in any way.

Hardening and strengthening of cementitious materials ensue from a joint development of complex physical and chemical processes. The deriving energy of these processes is the chemical reaction of hydration as well as the hydrolyzation of the mineral binders (cement, gypsum, lime, etc.) present in the material. As soon as a sufficient amount of product resulting from these reactions is accumulated per volume unit, a capillary-porous structure begins to form, first as a coagulation structure (long-range and short-range), and thereafter as colloidal and crystallization structures.

While at the beginning of the development of the hydration and hydrolysis the properties acquired by the material are reversible, once short-range coagulation structure is formed, the properties of the material become irreversible.

The reason of the reversibility at the beginning of the development of the hydration and hydrolysis is the long-range coagulation structure of the material. This structure features thixotropic properties which allow for reverse processes, e.g., under application of certain mechanical action, to occur. On the other hand, in the short-range coagulation structure, the formation of the initial crystalline frame finalizes all mechanical transitions within the material hence preventing reverse processes from occurring.

Thus, the crystallization strengthening process deterministically evolves from the initial conditions set at the time of short-range coagulation structure formation. As these initial conditions depend on the mechanical state of the material when its structure still has a long-range nature, it is appreciated that mechanical transitions occurring at that time substantially determine the subsequent crystallization of the material, hence also its strength.

Referring now to the drawings, FIG. 1 is a flowchart diagram of a method suitable for determining a setting period of a chemically-active material, according to various exemplary embodiments of the present invention.

It is to be understood that, unless otherwise defined, the method steps described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and proceeds to 11 at which an electrical property of the material is measured so as to provide a time-dependence of the property. In various exemplary embodiments of the invention the electrical property is measured continuously. The electrical property is preferably the electrical resistivity $\rho$ of the material, but can also be a proxy of the electrical resistivity, for example, electrical resistance, electrical impedance (real and/or imaginary part), electrical conductivity, electrical conductance and the like. The ordinarily skilled person would appreciate that while the resistivity and conductivity are specific properties which depend on the type of the material and its thermodynamic state but not on its shape and size, the resistance and conductance are non-specific measures which depend on the type, thermodynamic state, shape and size of the material. For a given shape and size of the material, a specific property can always be determined from a non-specific measure, and vice versa.

The electrical property can be measured by any procedure known in the art. Preferably, the electrical property is measured by direct contact with the material. Namely, two or more electrodes are brought to a physical contact with the material and a voltage is applied between the electrodes to thereby measure the electrical property. In a preferred embodiment, the electrical property is measured by generating an electric field between the electrodes along a sufficiently long contour within the material. Typically, the contour has a length which is at least two times the distance between the electrodes. In various exemplary embodiments of the invention the electrical property is measured in a constant volume. It was unexpectedly found by the present inventor that the use of sufficiently long contour within the material allows the identification of transitions which are unidentifiable by other techniques. A preferred device for measuring the electrical property using a sufficiently long contour is described hereinunder.

Figure 2:
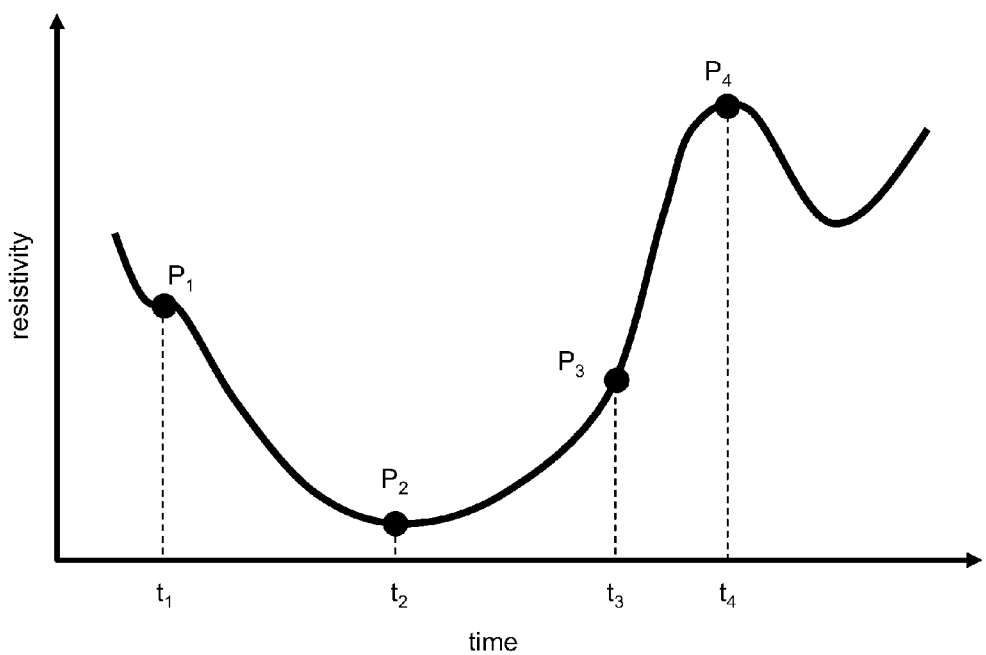
FIG. 2 is a schematic illustration of a time-dependence of the electrical resistivity of a chemically-active material, measurable according to the teachings of some embodiments of the present invention.

FIG. 2 is a schematic illustration of a time-dependence of the electrical resistivity of a chemically-active material, measurable according to the teachings of some embodiments of the present invention. Shown in FIG. 2 are several identifiable transition points ($P_1$-$P_4$). As will be explained below, the method of the present embodiments is capable of identifying at least a few of these points on the time-dependence and associate state transitions of the material for each identified point. In various exemplary embodiments of the invention one or more, preferably all, the transition points are identified on a linear scale of the resistivity curve. In various exemplary embodiments of the invention one or more, preferably all, the transition points are identified using a moving time-window having a width of about 2 hours.

In some embodiments of the present invention the method proceeds to 12 at which a transition from a first workable state of the material to a second workable state is identified using the time dependence. In this transition, the amount of physically bound water in the material abruptly drops due to formation of chemically bounds between water molecules and the solid phase. Traditionally this transition is identified by a slump test, wherein an abrupt slowing of slump is observed. For example, in the first workable state, when the amount of physically bound water is relatively high, the typical slump is about 16-20 cm, and in the second workable state, when the amount of physically bound drops, the typical slump is less than 6 cm. In conventional analysis techniques, once such abrupt slowing of slump is observed, the slump test is replaced by the VeBe test. Thus, the present embodiments are capable of identifying a transition which is equivalent to an abrupt slowing of slump that would have been observed had the material been subjected to a slump test.

The transition between the two workable states is preferably associated with a point of inflection of the resistivity curve (see point $P_1$ in the exemplified illustration of FIG. 2).

In this embodiment, the time of transition is defined as the time $t_1$ which corresponds to point $P_1$.

In some embodiments of the invention the method proceeds to 13 at which a transition from workable state of the material (typically the aforementioned second workable state) to a non-workable state of the material is identified. Traditionally this transition is identified by the VeBe test, wherein a plateau of VeBe times is observed. In conventional analysis techniques, once such plateau is observed, the VeBe test is replaced by the Proctor needle test.

The transition between the workable and non-states is preferably associated with a point of local minimum of the resistivity curve (see point $P_2$ in the exemplified illustration of FIG. 2). In this embodiment, the time of transition is defined as the time $t_2$ which corresponds to point $P_2$.

In some embodiments of the present invention the method proceeds to 14 at which the method identifies the setting-start of the material. The setting-start is preferably associated with the onset of a fastest rise of the resistivity curve (see point $P_3$ in the exemplified illustration of FIG. 2). In this embodiment, the setting-start time is defined as the time $t_3$ which corresponds to point $P_3$.

In some embodiments of the present invention the method proceeds to 15 at which the method identifies the setting-finish of the material. The setting-finish is preferably associated with local maximum of resistivity (see point $P_4$ in the exemplified illustration of FIG. 2). In this embodiment, the setting-finish time is defined as the time $t_4$ which corresponds to point $P_4$.

In some embodiments of the present invention the setting-start time can be defined as the average between the time $t_2$ corresponding to the local minimum of the resistivity (point $P_2$) and the time $t_4$ corresponding to the local maximum of the resistivity (point $P_3$). Thus, in these embodiments the setting-start equals $(t_2+t_4)/2$, and the setting-finish equals $t_4$.

Once the setting times are determined, the setting period is defined as then period between the setting-start time and setting-finish time.

When the material is concrete, each of the transitions corresponding to points $P_1$-$P_4$ above is preferably identified while the age of the concrete is below 24 hours.

The present embodiments also contemplate identification of other transitions, such as, but not limited to, transition from a gel state and a capillary-porous colloidal state, transition from a capillary-porous colloidal state to a colloidal-crystalline state and transition from a discontinuous crystalline state to a continuous crystalline state. These operations are collectively shown by Block 16 of FIG. 1 and can be executed by any procedure known in the art. For example, part or all the procedure disclosed in U.S. Pat. No. 7,225,682 supra can be employed. A representative demonstration for the identifications of these transitions is provided in the Examples section that follows.

In some embodiments of the present invention the method proceeds to 17 at which the compressive strength is determined, based, at least in part, on the time-dependence. This can be done by any procedure known in the art, such as, but not limited to, the procedure disclosed in U.S. Pat. No. 7,225,682 or part thereof. A preferred procedure for determining the compressive strength is provided hereinunder.

The method ends at 18.

The advantage of the present embodiments is that, unlike other published techniques, the identification of various transitions is performed directly from the time-dependence of the resistivity curve. For example, in the technique described by Li et al. supra, points which are identified on the resistivity curve are only indirectly related (via a phenomenological linear relationship) to the setting times.

Figure 3:
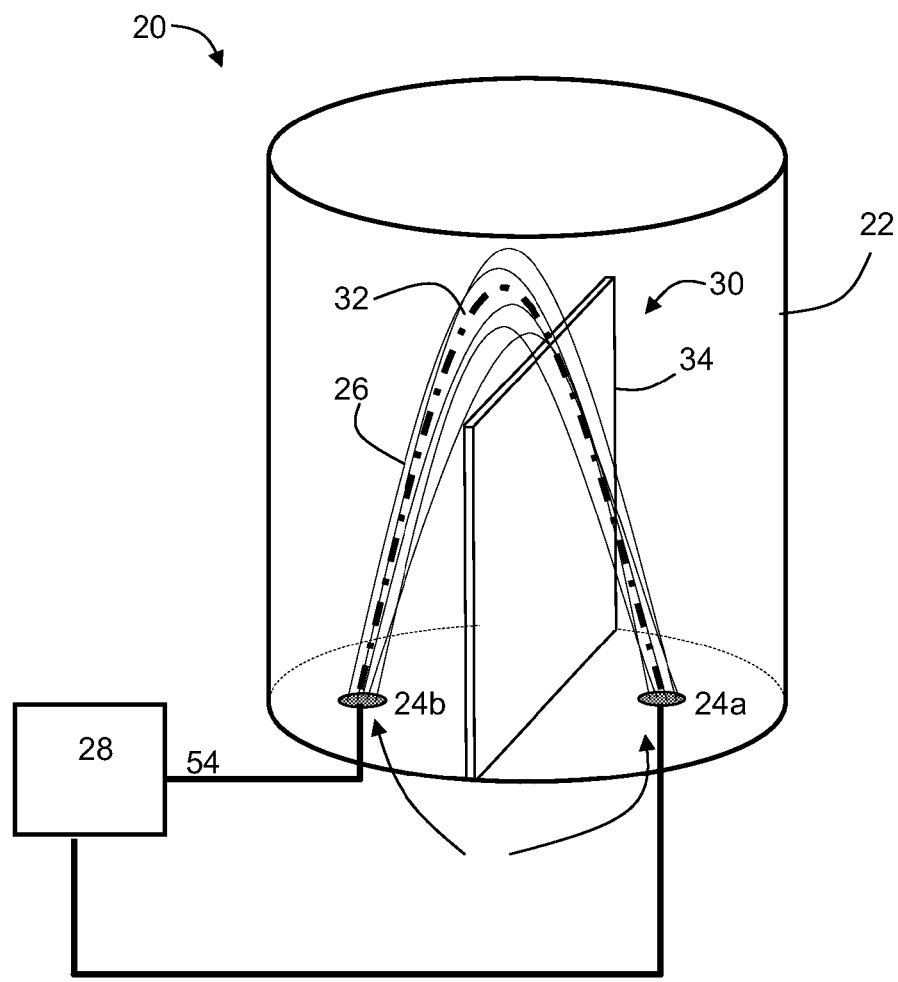
FIG. 3 is a schematic illustration of a measuring apparatus, according to various exemplary embodiments of the present invention.

Reference is now made to FIG. 3 which is a schematic illustration of a measuring apparatus 20, according to various exemplary embodiments of the present invention. Apparatus 20 can be employed by the method described above for measuring the electrical property of a chemically-active material. Apparatus 20 comprises a container 22 for holding the chemically-active material and at least two electrodes 24. Electrodes 24 serve for generating an electric field 26 within the chemically-active material, and sensing the resistance of the chemically-active material to electric field 26. The generation of electric field 26 can be done by connecting electrodes 24 to a voltage source 28, via lead 54. The resistance of the chemically-active material can be sensed by measuring a particular component (real-part or imaginary part) of electrical current flowing through electrodes 24.

According to a preferred embodiment of the present invention apparatus 20 further comprises a contouring device 30 for contouring electric field 26 substantially along a predetermined contour 32 within the chemically-active material. The contouring of electric field 26 along contour 32 ensures that the density of current which is provided by electrodes 24 is substantially constant at all times, hence facilitating a highly reliable measurement. Preferably, but not necessarily, contouring device 30 is a passive contouring device. For example, as shown in FIG. 3, contouring device 30 can comprise a dielectric partition 34, positioned between a first electrode 24a and a second electrode 24b. In some embodiments of the present invention a size and shape of partition 34 is selected such that the electric field lines bypass partition 34 hence being contoured along contour 32. A preferred shape of partition 34 is a plane having a diameter similar to the diameter of container 22 and a height which is about 75% of the height of container 22. For example, when container 22 is a cylinder, about 10 cm in diameter and about 16 cm in height, partition 34 is a plane having dimensions of about 10 cm wide and about 8 cm height. It is to be understood that these values are not to be considered as limiting.

Also contemplated is the use of an active contouring device, such as the active contouring device disclosed in U.S. Pat. No. 7,225,682 supra.

Figure 4:
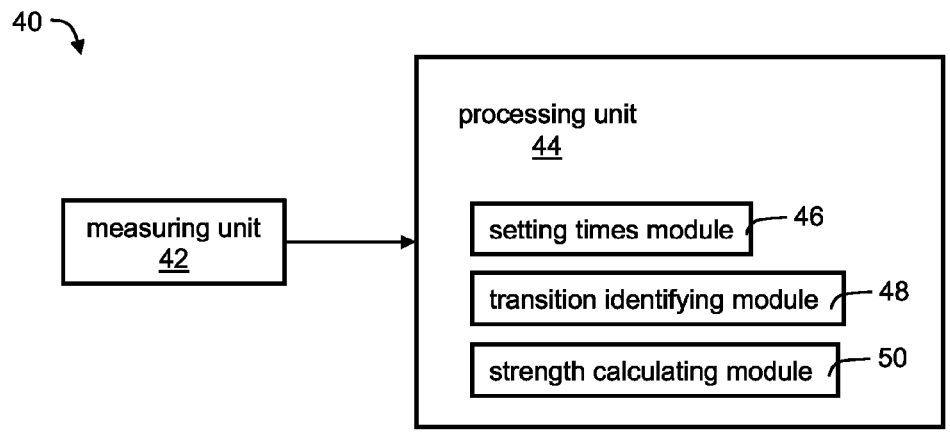
FIG. 4 is a schematic illustration of a system suitable for determining setting period of a chemically-active material, according to various exemplary embodiments of the present invention.

Reference is now made to FIG. 4 which is a schematic illustration of a system 40 suitable for determining setting period of a chemically-active material, according to various exemplary embodiments of the present invention. System 40 comprises a measuring unit 42, for continuously measuring the electrical property of the material as further detailed hereinabove. Unit 42 is preferably configured to measure the electrical property by direct contact with the material. For example, unit 42 can comprise apparatus 20 for generating an electric field between two electrodes along a sufficiently long contour within the material, as further detailed hereinabove.

System 40 further comprises a processing unit 44, which extracts the time-dependence of the electrical property. Unit 44 can be, for example, a special data processor or a special computer. In various exemplary embodiments of the invention unit 44 is configured for defining, based on the time-dependence, the setting-start and/or setting-finish times of the material. Thus, processing unit van comprise a setting times module 46 which designed and configured for defining the setting-start time and setting-finish time, as further detailed hereinabove.

Unit 44 can also identify one or more other transitions based on said time-dependence, such as, but not limited to, transition between the first and second workable states, transition between the workable and non-workable states. Thus, processing unit can comprise a transition identifying module 48, which is designed and configured for identifying transition between the first and second workable states and/or transition between the workable and non-workable states, as further detailed hereinabove. Module 48 can also be configured for identifying one or more other transitions, e.g., from gel to capillary-porous colloidal state and/or from capillary-porous colloidal state to colloidal-crystalline state and/or from discontinuous crystalline state to continuous crystalline state.

In various exemplary embodiments of the invention unit 44 is also configured for determining a compressive strength of the material. Thus unit 44 can comprise a strength calculating module, which is designed and configured for calculating the compressive strength of the material as further detailed hereinbelow.

A particular feature of some embodiments of the present invention is the ability to monitor the strengthening process of the chemically-active material during the stage in which the properties of the material can still be adjusted, according to the needs of the specific application for which the chemically-active material is manufactured. Once the chemically-active material passes the reversible stage it enters the irreversible stages of hardening, in which the manufacturer's control on the quality of the final product is very limited. In is known that during the irreversible hardening stages, the compressive strength, S, as a function of time, t, has a logarithmic shape:

$$S(t) = S_n \frac{\log t}{\log n}, \quad \text{(EQ. 1)}$$

where $S_n$ denotes the compressive strength of the material at time t=n.

According to a some embodiments of the present invention, the measuring of the electrical property is initiated sufficiently before the compressive strength of the chemically-active material develops a logarithmic time-dependence. For concrete, for example, a preferred age of the mix at which the measurement is initiated is below about 2 hours.

One ordinarily skilled in the art would appreciated that monitoring the strengthening process of concrete at such an early stage is extremely advantageous, because in this stage the concrete manufacturer is provided with a sufficient time to adjust the preparation process according to its needs before the mix enters the aforementioned irreversible hardening stages.

In some embodiments of the present invention the time-dependence of the electrical resistivity is correlated with the compressive strength so as to obtain a correlation function. The correlation function can be realized in more than one way. Thus, in some embodiments, the correlation function has an analytical form, in some embodiments the correlation function has a numerical form (e.g., a table) and in some embodiments the correlation function has a graphical form (a calibration curve).

The correlation function can be used for parameterizing the logarithmic time-dependence of S(t), characterizing the development of the compressive strength at the later hardening stages. More specifically, denoting the correlation function by $\phi$, the value of S(t) can be calculated using the following equation:

$$S(t) = \phi[\rho(t)], \quad \text{(EQ. 2)}$$

form which the parameterization of Equation 1 can be obtained by selecting an appropriate initial time, n, and calculating $S_n = S(t=n)$. In other words, once $\phi$ is known, the compressive strength of the chemically-active material, substantially at all times in which the material has a liquid phase, can be calculated using the following equation:

$$S(t) = \begin{cases} \varphi[\rho(t)] & \tau \leq n \\ S_n \frac{\log t}{\log n} & \tau > n. \end{cases} \quad \text{(EQ. 3)}$$

Alternatively, the same function $\phi$ can be used for calculating the compressive strength of the material at all times. This can be done by determining the correlation function during a stage in which the compressive strength of the chemically-active material already has a logarithmic time-dependence. For example, several mechanical measurements of compressive strength can be performed, say, when the age of the material is above 50 or above 100. These measurements can be correlated (e.g., using linear regression or another fitting procedure) with electrical measurements performed in accordance with some embodiments of the present invention at times, to provide the correlation function $S=\phi(\rho)$. Such correlation function can be used for determining the strength at all times.

Thus, the present embodiments successfully provide a technique suitable for monitoring the compressive strength of the chemically-active material at any age (e.g., at least a month or at least a year or at least five years or at least 10 years or at least 15 years, e.g., 20 years or more) of the material.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Determination of Setting Period and Transitions Prior to Setting-Finish

Embodiments of the present invention have been utilized for analyzing a B-30 concrete modified by the following admixtures: retarder (0.002 C) and water reducer (0.015 C) with W/C=0.68, and a maximum coarse aggregate size of 14 mm. In the present Example, the setting-start time was defined as the time corresponding to the onset of a fastest rise of the resistivity curve, and the setting-finish time was defined as the time corresponding to the local maximum of resistivity curve. In addition, transitions which occurred prior to the setting-finish time were also identified.

Resistivity measurements according to the teachings of the present embodiments were conducted using the apparatus shown in FIG. 3. For comparison, the following mechanical tests were also conducted: slump test, VeBe test and Proctor needle test. A 5 inch slump was employed for the slump and VeBe test.

The measurements of resistivity were substantially continuous. The mechanical tests were performed at a rate of about 4 measurements per hour. The slump tests were performed at the first 3 hours, the VeBe test were performed when the age of the concrete was between 3 and 10 hours and the Proctor needle tests were performed when the age of the concrete was between 10 and 20 hours. Additionally, strength tests were performed at 24, 48, 72, 168 and 672 hours.

All samples for the mechanical tests as well as the electrical resistivity measurements were prepared from the same concrete batch. The samples were stored in the same conditions during the entire experiment.

Figure 5:
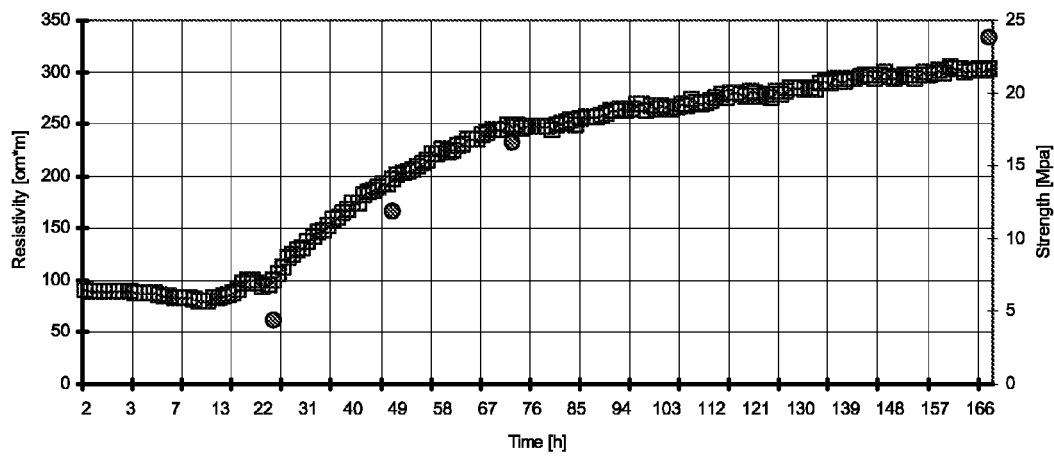
FIG. 5 shows resistivity (open squares) and strength (filled circles) as a function of the time in hours as measured in experiments conducted according to some embodiments of the present invention.

FIG. 5 shows the resistivity (open squares) and strength (filled circles) as a function of the time in hours for the period of 2-168 hours. The resistivity values are marked on the left ordinate in units of $\Omega \cdot m$ and the strength values are marked on the right ordinate in units of MPa. Data for the period of 168-672 hours not shown. As a representative example, after 28 days (672 hours) the measured resistivity was 455 $\Omega \cdot m$ and the strength was 35.5 MPa.

The results in FIG. 5 demonstrate that there are two main stages of hardening: a first stage in which the change in resistivity is moderate, and a second stage in which the change in resistivity is more pronounced. As shown, the transition between stages occurs at about 24 hours.

As will be demonstrated below (see FIG. 6B), in the first stage the resistivity curve is non-monotonic as a result of a joint development of chemical and structural transformations. In this stage, chemical processes are initially dominant, and resistivity declines as a result of an increase in the concentration of positively charged ions. Later, when the concentration of reaction products increases, the thickness of water layers decreases and ion mobility falls off, leading to stabilization and then an increase in resistivity. During the beginning of the first stage, the concrete is a visco-plastic material capable of thixotropic dilution, which makes it workable. Shortly before the setting-start, the concrete becomes less or non-workable. During the setting period, coagulation and subsequently initial crystallization structures are formed.

The second stage is the crystallization strengthening of the concrete. It is characterized by monotonous changes in the resistivity. The time-dependence of the resistivity during the second stage is logarithmic.

Figure 6A:
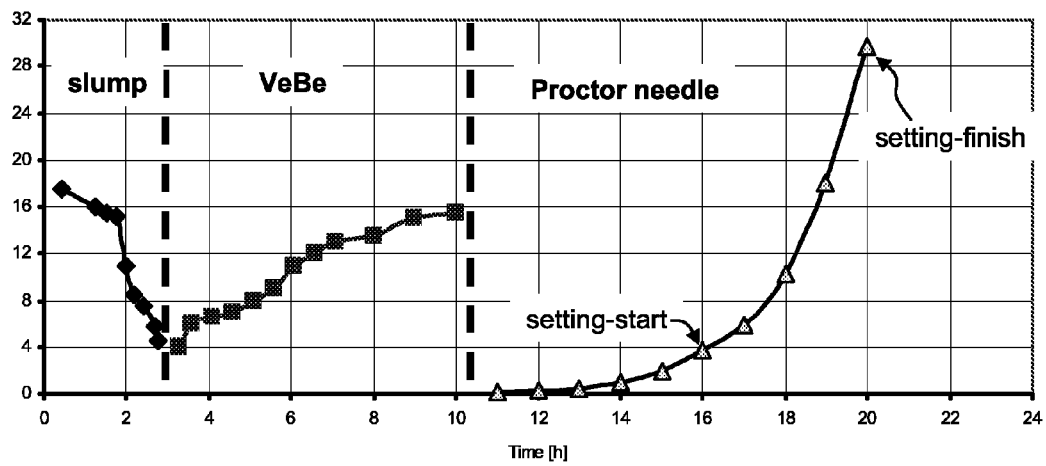
FIGS. 6A-B show the results of the mechanical tests (FIG. 6A) and the resistivity measurements (FIG. 6B) as performed in accordance with some embodiments of the present invention, over an interval of 24 hours.
Figure 6B:
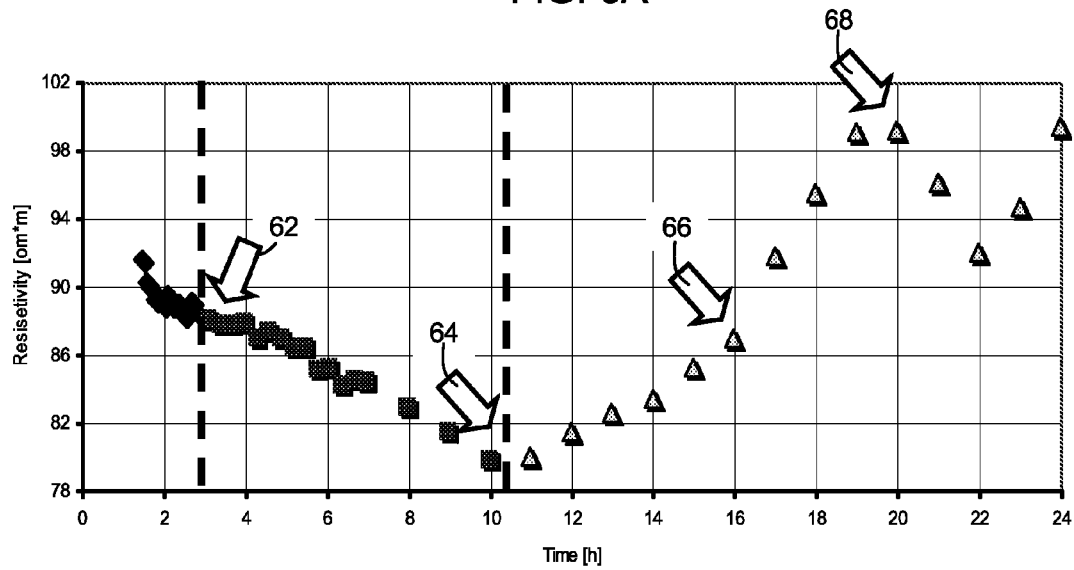

FIGS. 6A and 6B show the results of the mechanical tests (FIG. 6A) and the resistivity measurements (FIG. 6B) as performed in accordance with some embodiments of the present invention, over an interval of 24 hours. For clarity of presentation, all the results of the mechanical tests are shown on the same plot. In FIG. 6B, different symbols mark to different time intervals (dark square for the time interval at which the slump test was performed, gray square for the time interval at which the VeBe test was performed, and triangles for the time interval at which the Proctor needle test was performed) but they all correspond to the same type of measurement (resistivity). The different intervals are separated by dash lines in FIGS. 6A-B.

A comparison between FIG. 6A and FIG. 6B demonstrates that changes in the structural-moisture state at the early stage of the concrete hardening are identifiable directly from the electrical resistivity curve, without the need for further correlation.

For example, a substantially abrupt slowing of slump (from 17.5 cm to 4.5 cm) is completed at t=2.75 hours (FIG. 6A). This transition is identified on the resistivity curve as a point of inflection (marked by block arrow 62) A subsequent decrease in the resistivity up to its minimum value at t=10.0 hours (FIG. 6B, block arrow 64) corresponds to a change in consistency measured in the viscometer of the VeBe test (FIG. 6A). Following a short stabilization period, the electrical resistivity begins to grow (FIG. 6B). This is consistent with the beginning of the setting process as seen in FIG. 5.

The start and finish of the setting as determined by the standard Proctor method (ASTM C-403) were at t=15.75 hour and t=19.8 hours, respectively. These times can be identified directly from the resistivity curve of the present embodiments. The setting-start is identified as the point marking the onset of the fastest increase in the resistivity. This onset was observed at t=15.97 hours (FIG. 6B, block arrow 66). The setting-finish is identified as the local maximum of the resistivity curve. This onset was observed at t=19.52 hours (FIG. 6B, block arrow 68).

This experiment demonstrates that the workability and setting times of concrete mix can be determined by continuous measurements of electrical resistivity or a proxy thereof during the first 24 hours of hardening. This can allow the constructor to accurately select the additives and water content of the mix so as to achieve the desired workability and setting times.

Figure 7:
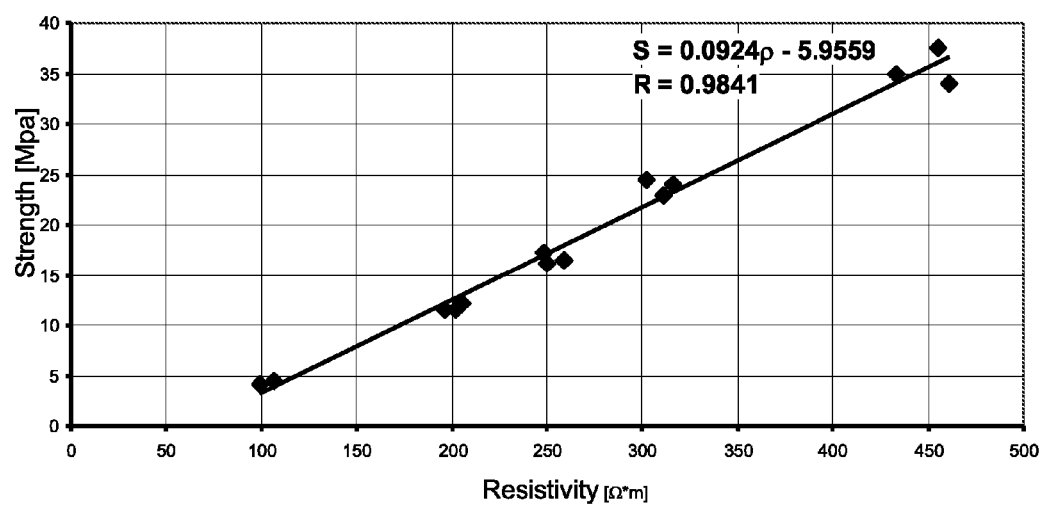
FIG. 7 shows correlation between strength and electrical resistivity as measured in accordance with some embodiments of the present invention during the first 500 hours.

The correlation between the strength as measured by standard strength tests and the electrical resistivity as measured in accordance with some embodiments of the present invention during the first 500 hours is shown in FIG. 7. As shown, a linear correlation was observed. A linear regression procedure was used for determining the following relation between the strength S and resistivity ρ, with Pearson $R^2$ of 0.9841:

$$S(\rho)=0.0924\rho-5.9559.$$

Example 2

Determination of Setting Period Using the Average Embodiment

Embodiments of the present invention have been utilized for determining the setting periods of various concrete mixes. In the present example, the setting-start time was defined as the average between the time corresponding to the local minimum of the resistivity and the time corresponding to the local maximum of the resistivity. The setting finish time was defined as the time corresponding to the local maximum of the resistivity.

12 concrete mixes (mix Nos. 1-12) were tested. The following cement types were used: CEM II 42.5N for mix Nos. 1-8, 11 and 12, and CEM II 52.5N for mix Nos. 9 and 10. The batch used for mixes 1-6, 11 and 12 was different than the batch used for mixes Nos. 7 and 8.

The mixes included quarry sand (QS) and sea sand (SS), at various densities and ratios. Some mixes (mix Nos. 1-4) included additional aggregates which were measured by saves of sizes 19 mm, 14 mm, 5 mm, 9 mm and 2.36 mm. Hereinunder, the notation X/Y in connection to aggregate means that the aggregate passes through sieve of size X but not through a sieve of size Y. Namely, the size of the aggregate is larger than Y and smaller than X.

Mix No. 1 was tested with full composition of the concrete mix. Mix No. 2 was tested according to ASTM C-403: all grains above ¾" were removed from the mix. Mixes Nos. 11 and 12 were modified by the additives Redycret-5 (3.96 kg/m³) and Hostopur (0.014 kg/m³).

The concrete mixes were subject to curing either in an oven at a temperature of 30° C. (for mix Nos. 1, 2, 4, 6, 8, 10 and 12) or at room temperature of 20° C. (for mix Nos. 3, 5, 7, 9 and 11).

The setting times were determined both using the resistivity curve, in accordance with some embodiments of the present invention and using a Proctor needle test.

Table 1 below summarizes the results. In Table 1, W/C denotes the amount of cement (C) and water (W), Pr denotes results obtained via Proctor needle test and ρ denotes results obtained using the resistivity curve.

TABLE 1

| | | mix composition [Kg/m³] | | | | | setting time [min] | | | |
| | | aggregates | | | sand | | start | | finish | |
| No. | W/C | 19/14 | 14/5 | 9/2.36 | QS | SS | Pr | ρ | Pr | ρ |
|---|---|---|---|---|---|---|---|---|---|---|
| 1 | 161/280 | 267 | 539 | 444 | 576 | 95 | | 276 | | 444 |
| 2 | 161/280 | 267 | 539 | 444 | 576 | 95 | 284 | 272 | 409 | 432 |
| 3 | 195/300 | — | — | 1010 | 694 | 127 | | 382 | | 614 |
| 4 | 195/300 | — | — | 1010 | 694 | 127 | 252 | 262 | 405 | 434 |
| 5 | 252/360 | — | — | — | 1332 | 290 | | 408 | 641 | 666 |
| 6 | 252/360 | — | — | — | 1332 | 290 | 336 | 308 | 472 | 492 |
| 7 | 252/360 | — | — | — | 1332 | 290 | 310 | 328 | 558 | 548 |
| 8 | 252/360 | — | — | — | 1332 | 290 | 272 | 258 | 411 | 426 |
| 9 | 252/360 | — | — | — | 1332 | 290 | 285 | 274 | 471 | 476 |
| 10 | 252/360 | — | — | — | 1332 | 290 | 261 | 259 | 389 | 392 |
| 11 | 252/360 | — | — | — | 1330 | 289 | 443 | 423 | 634 | 681 |
| 12 | 252/360 | — | — | — | 1330 | 289 | 368 | 325 | 509 | 518 |

Table 1 demonstrates that the procedure of the present embodiments is capable of determining the setting period to a high level of confidence. The correlations between the setting times as obtained via Proctor needle test and using the resistivity curve are: $t_{Pr}=0.916\ t_\rho+18.732$ with Pearson $R^2=0.9026$ for setting-start time, and $t_{Pr}=1.0478\ t_\rho-6.9204$ with Pearson $R^2=0.9765$ for setting-finish time, where $t_{Pr}$ denotes a setting time measured via Proctor needle test and $t_\rho$ denotes a setting time measured in accordance with the present embodiments.

Example 3

Determination of Other Transitions and Strength Predictions

Measurements of electrical resistivity were performed on different samples of cement, according to some embodiment of the present invention. The following measurements were continuously taken when the age of the mix was below 48 hours.

Figure 8:
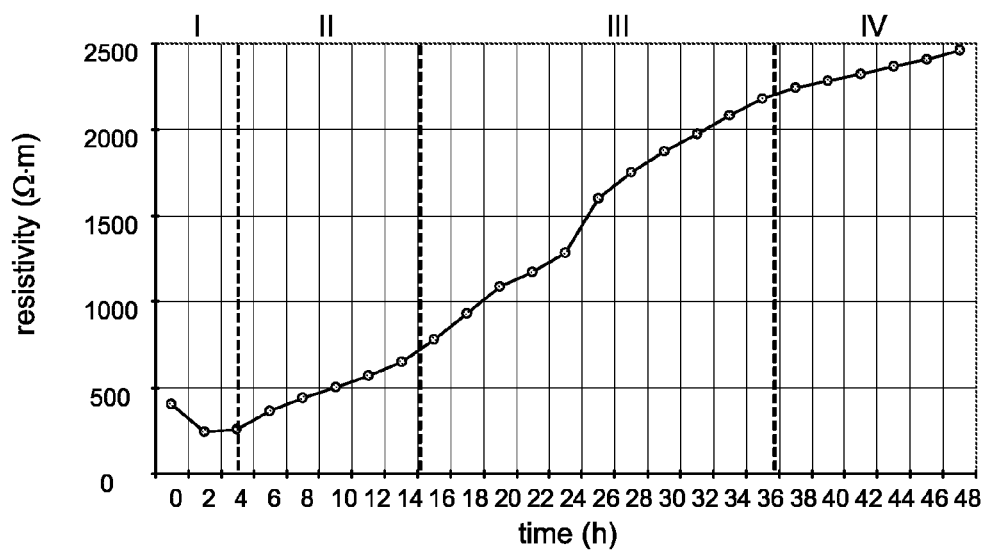
FIG. 8 shows electrical resistivity as a function of the time in hours, as measured in experiments conducted according to some embodiments of the present invention.

FIG. 8 shows the electrical resistivity, ρ, in units of Ω·m, as a function of time, t, in hours, as measured for a standard cement-sand mix (according to the EU standard EN-196, Part 1: Methods of testing cement; Determination of strength"). The mix was prepared using CEM-1 Type cement, strength class 42.5 N (EU standard EN-197, Part 1: "Composition, specification and conformity criteria for common cements").

In accordance with some embodiments of the present invention, a time-dependence of the resistivity was extracted and functional transitions of the time-dependence were identified.

As used herein "functional transition" refers to any detectable mathematical transition of a function, including without limitation, a transition of a given function (e.g., a change of a slope, a transition from increment to decrement or vice versa) and a transition from one characteristic functional behavior to another (e.g., a transition from a linear to a nonlinear behavior or a transition from a first nonlinear behavior to a second, different, nonlinear behavior).

The functional transitions can be identified, for example, by calculating a derivative of the time-dependence and finding zeros thereof. As will be appreciated by one of ordinary skill in the art, whenever a transition of a function is characterized by a zero of one of its derivatives. For example, a transition from increment to decrement or vice versa is characterized by a zero of a first derivative, a transition from a concave region to a convex region or vice versa (points of inflection) is characterized by a zero of a second derivative, etc. According to a preferred embodiment of the present invention any derivative of the time-dependence can be used. Generally, the functional transitions are preferably characterized by a sign inversion of an nth derivative of time-dependence, where n is a positive integer.

Additionally or alternatively the functional transitions can be identified by observing deviations of the time-dependence from smoothness. In this embodiment, the functional transitions can be identified either with or without calculating the derivatives of the time-dependence. For example, deviations from smoothness can be identified manually or by comparing the time-dependence to a known smooth function. This embodiment was employed in the present Example.

As demonstrated in FIG. 8, four structural states of the mix, were identified by inspecting the resistivity time-dependence, $\rho(t)$ and identifying the functional transitions. These states are a gel state (referred to in this example and in FIG. 8 as state I), a capillary-porous colloidal state (referred to in this example and in FIG. 8 as state II), a colloidal-crystalline state (referred to in this example and in FIG. 8 as state III) and continuous crystalline state (referred to in this example and in FIG. 8 as state IV).

Transitions between states were observed in the following values of t: 4 (transition from state I to state II), 15 (transition from state II to state III) and 37 (transition from state III to state IV). An additional functional transition in which the increment of resistivity is being moderated, was observed at the time interval between about 20 hours and about 25 hours. This transition characterizes the formation of three-dimensional cells, prior to the building up of a continuous crystalline frame, in which the electrical resistivity is stabilized, as further detailed hereinabove.

Figure 9:
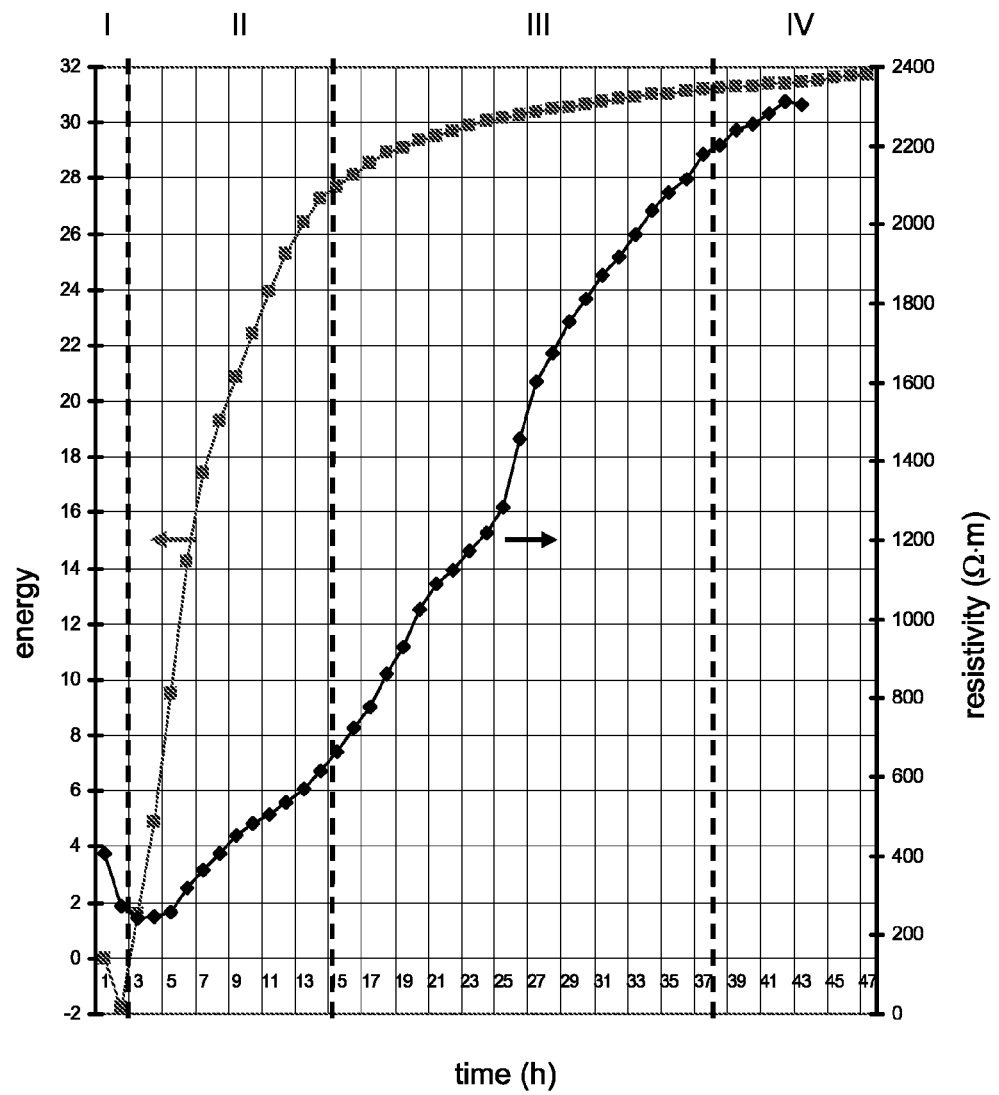
FIG. 9 shows a comparison between the energy of bound water, and the electrical resistivity, for the standard cement-sand mix, according to a preferred embodiment of the present invention.

FIG. 9 shows a comparison between the energy of the bound water, in units of J/s, and the electrical resistivity, for standard cement-sand mix. As shown, the electrical resistivity is more sensitive to transitions between the structural changes in the mix.

Figure 10:
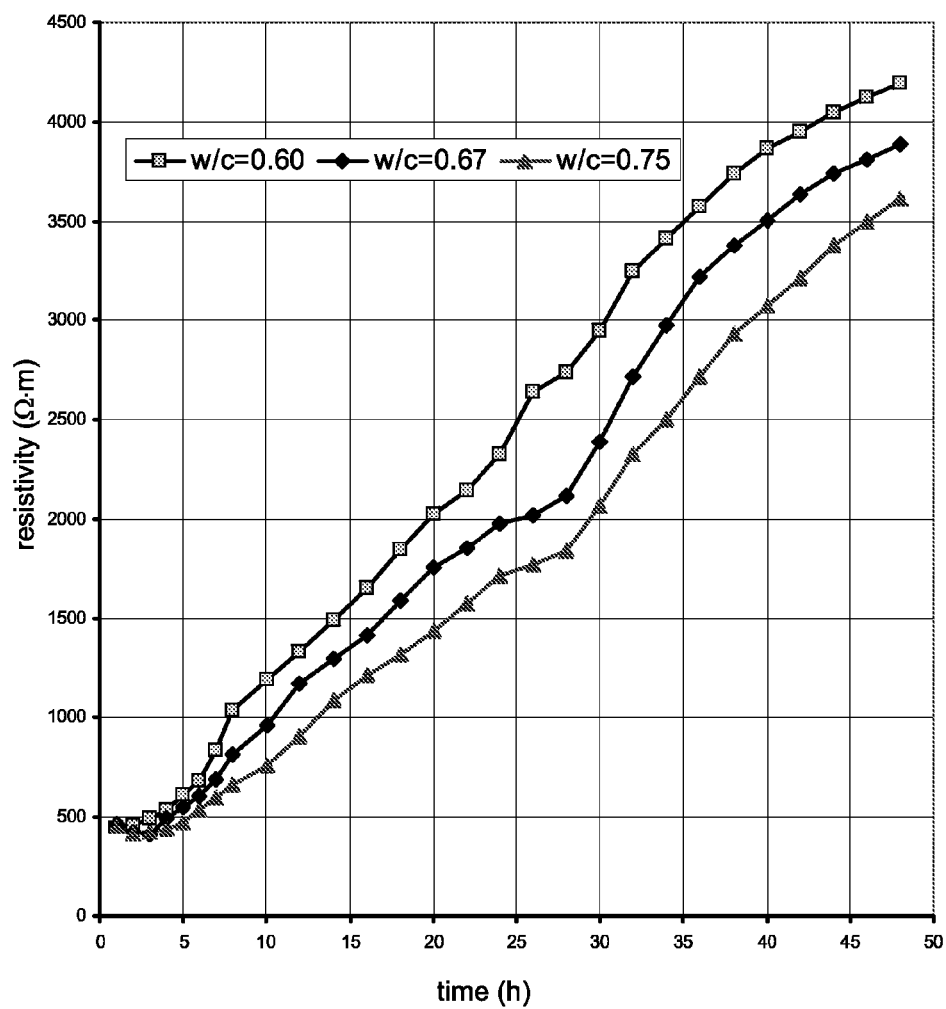
FIG. 10 shows the time-dependence of the electrical resistivity of a fine-grained concrete mix, using fine-grained dolomite aggregates purchased from Kohav-Ha-Shahar quarry, Israel.
Figure 11:
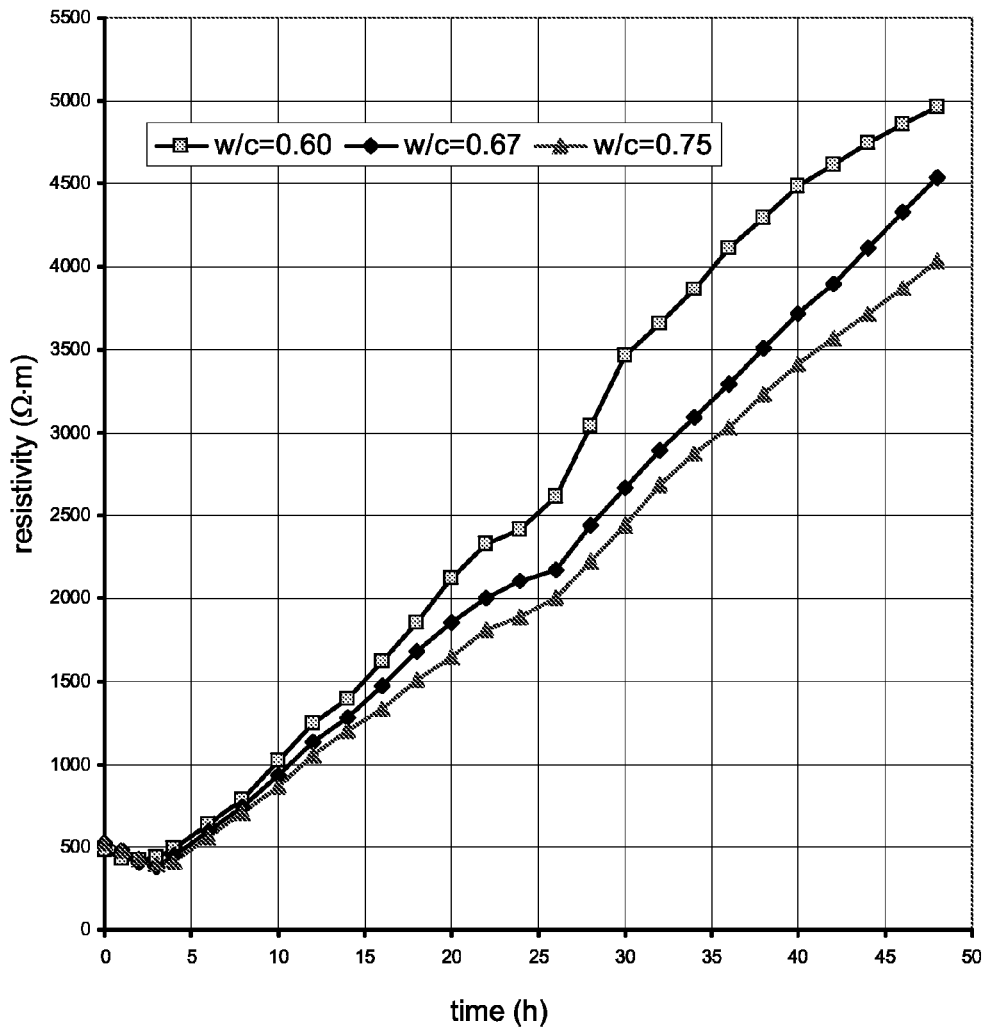
FIG. 11 shows the time-dependence of the electrical resistivity of a fine-grained concrete mix, using fine-grained dolomite aggregates purchased from Shfaram quarry, Israel.

FIG. 10 and FIG. 11 show the time-dependence of the electrical resistivity, $\rho(t)$, in units of $\Omega \cdot m$, of fine-grained concrete mixes, for water/cement ratios of 0.60, 0.67 and 0.75. The mixes were prepared using fine-grained dolomite aggregates purchased from Kohav-Ha-Shahar quarry, Israel (FIG. 10) and Shfaram quarry, Israel (FIG. 11), with a cement:send:aggregates composition of 1:2:3.

As shown in FIGS. 10-11, similar functional transitions were observed during the first 48 hours of hardening, irrespectively of the water/cement ratio or the type of aggregates. The functional transitions shown in FIGS. 10-11 are in agreement with the functional transitions of the standard cement-sand mix of FIG. 8 and FIG. 9. In addition, the fine-grained concrete mixes exhibits an increment moderation of $\rho(t)$, which characterizes the formation of three-dimensional cells in the third structural state of the mix. Similarly to the cement-sand mix, the moderation was observed approximately between t=20 hours and t=25 hours.

Figure 12A:
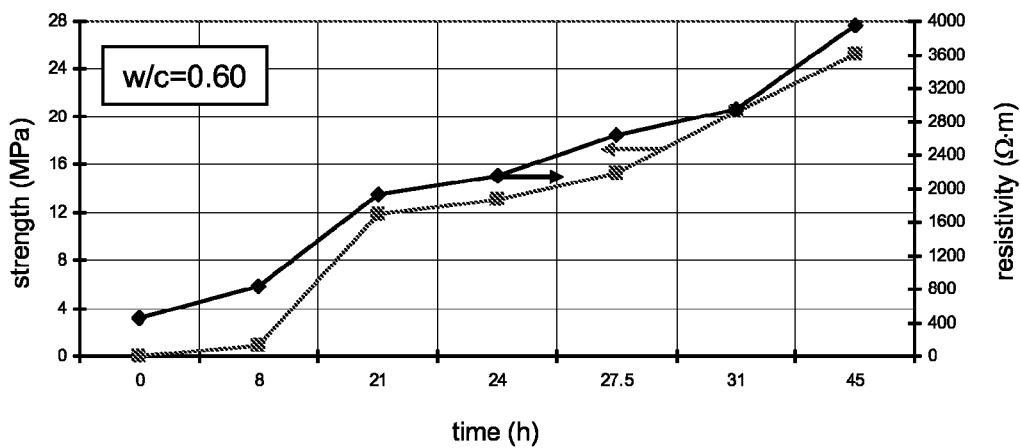
FIGS. 12A-C show comparisons between the time-dependences of the compressive strength and the electrical resistivity, of the fine-grained concrete mixes of FIG. 10, for water cement ratios of 0.60 (FIG. 12a), 0.67 (FIG. 12b) and 0.75 (FIG. 12c)
Figure 12B:
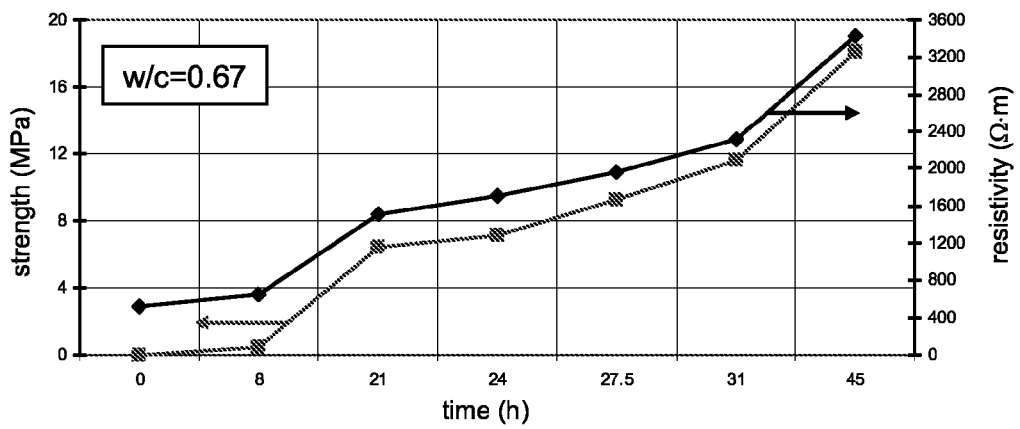
Figure 12C:
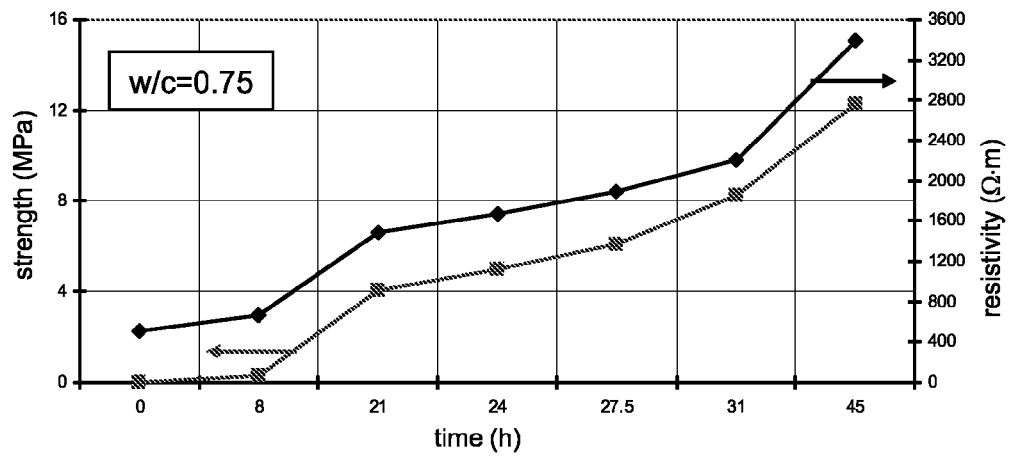
Figure 13A:
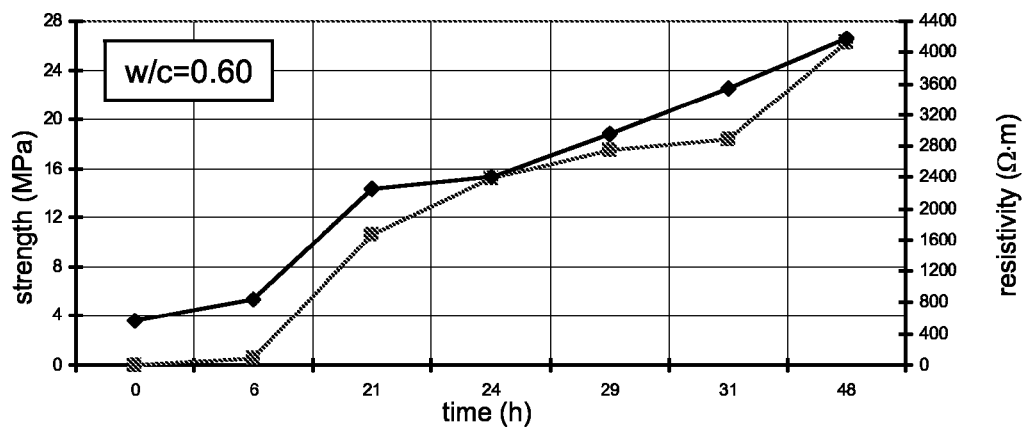
FIGS. 13A-C show comparisons between the time-dependences of the compressive strength, and the electrical resistivity of the fine-grained concrete mixes of FIG. 11, for water cement ratios of 0.60 (FIG. 13a), 0.67 (FIG. 13b) and 0.75 (FIG. 13c)
Figure 13B:
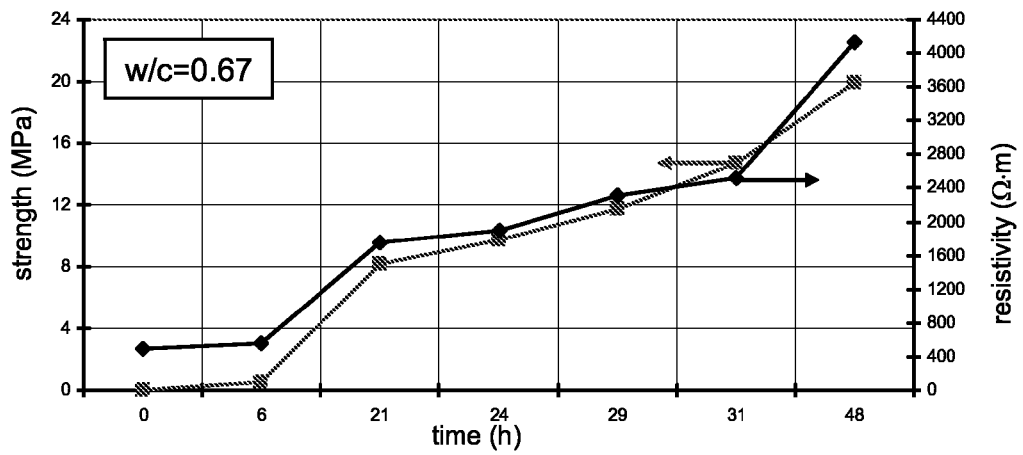
Figure 13C:
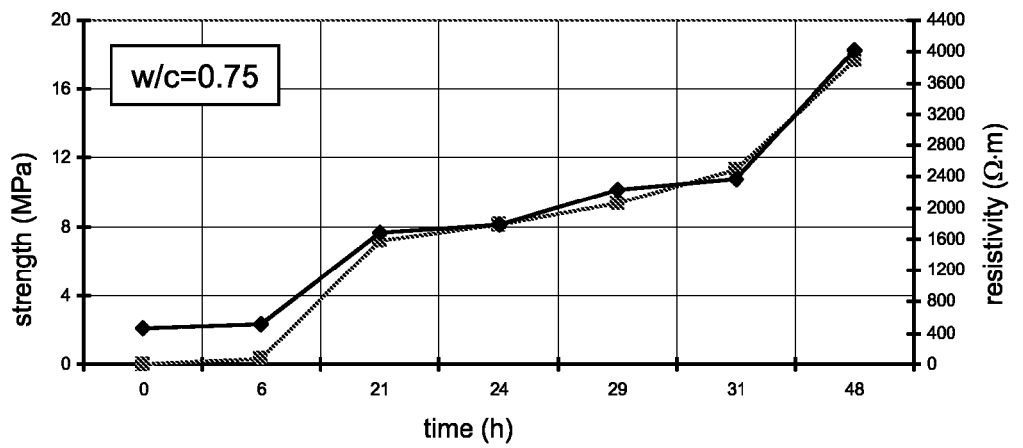

FIGS. 12A-C and FIGS. 13A-C show comparisons between the time-dependences of the compressive strength, R(t), in units of MPa, and the electrical resistivity, $\rho(t)$, in units of $\Omega \cdot m$, of the fine-grained concrete mixes of FIGS. 10 and 11, respectively. Shown are water/cement ratios of 0.60 (FIGS. 12A and 13A), 0.67 (FIGS. 12B and 13B) and 0.75 (FIGS. 12C and 13C). As shown in FIGS. 12A-13C, the curves R(t) and $\rho(t)$ exhibit similar behavior, in particular the increment moderation, observed approximately between t=20 hours and t=25 hours. Thus, in accordance with preferred embodiments of the present invention, functional transitions of $\rho(t)$ can be used for determining the strengthening state of the material.

Figure 14:
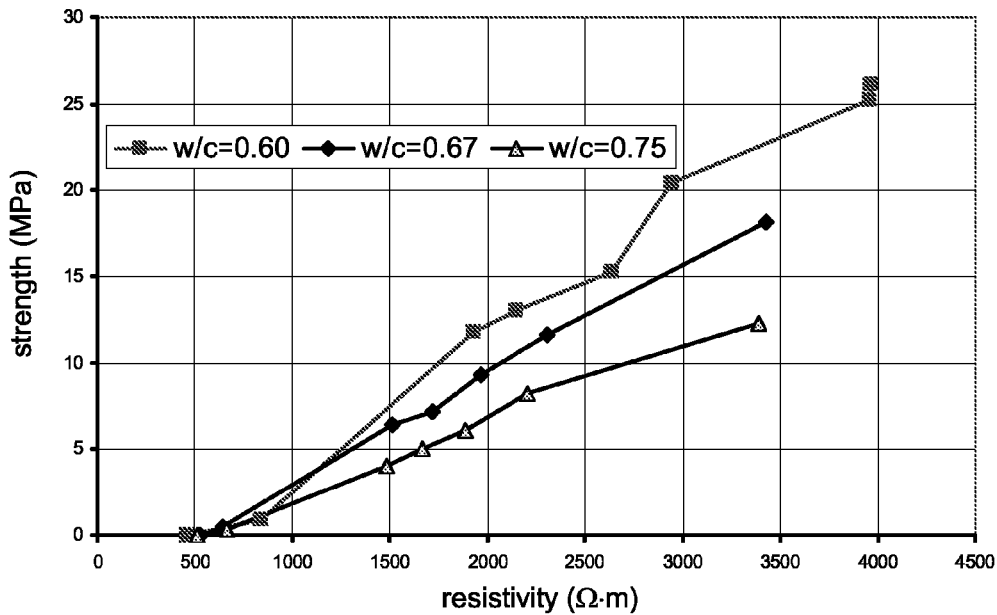
FIG. 14 show graphical representation of a correlation function, which correlate between the time-dependences of the electrical resistance and the compressive strength for the fine-grained concrete mixes of FIG. 10.
Figure 15:
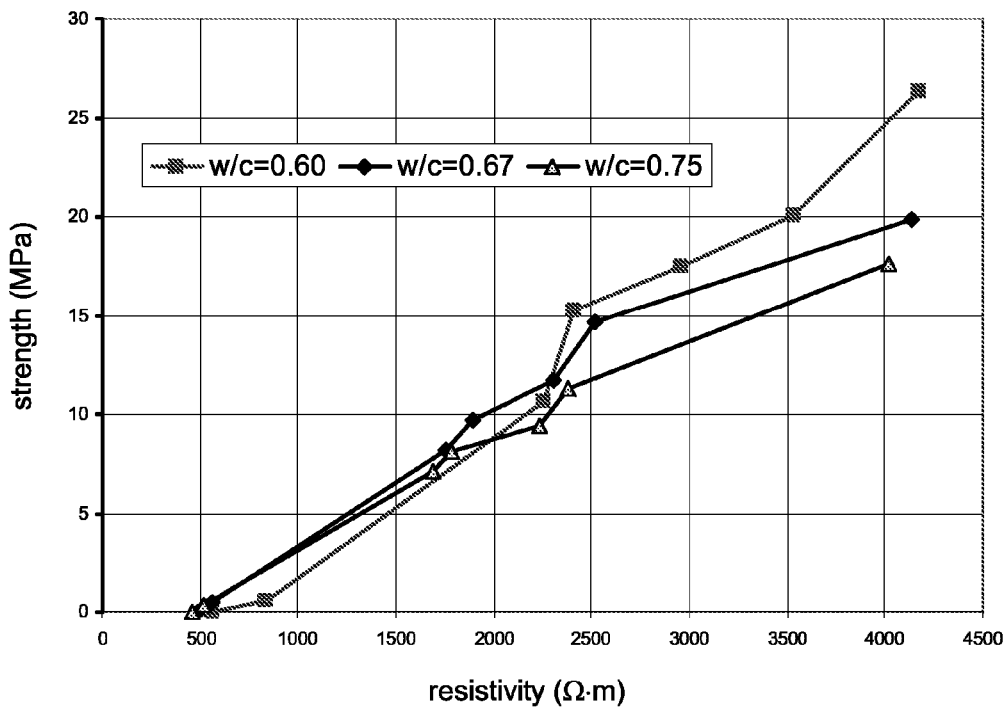
FIG. 15 show graphical representation of a correlation function, which correlate between the time-dependences of the electrical resistance and the compressive strength for the fine-grained concrete mixes of FIG. 11.

FIG. 14 and FIG. 15 show graphical representation of the correlation function, $\phi$, as determined by correlating between the time-dependences of the electrical resistance, $\rho$, and the compressive strength, R, at the early stages of hardening. FIG. 14 corresponds to the fine-grained concrete mix of FIG. 10, and FIG. 14 corresponds to the fine-grained concrete mix of FIG. 11. $\phi(\rho)$ can thus be used for determining the compressive strength, for different values of the electrical resistivity. For example, $\phi(\rho)$ can be used for determining the compressive strength at, say, t=50 hours, from which the compressive strength is known to have a logarithmic dependence.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining setting period of a chemically-active material, comprising:
   continuously measuring an electrical property of the material to provide a time-dependence of said property, said property being a resistivity or a proxy thereof; and
   using said time-dependence for defining a setting-start time and a setting-finish time, wherein said setting-start time is defined as a time of onset of a fastest rise of said resistivity and said setting-finish time is defined as a time of local maximum of said resistivity;
   thereby determining the setting period of the material.

2. The method of claim 1, further comprising using said time-dependence for identifying transition between a workable state of the material and a non-workable state of the material.

3. The method of claim 1, further comprising using said time-dependence for identifying transition between a first workable state of the material and a second workable state of the material, said transition being equivalent to an abrupt slowing of slump that would have been observed had the material been subjected to a slump test.

4. The method of claim 1, further comprising using said time-dependence for identifying transition between a gel state of the material and a capillary-porous colloidal state of the material.

5. The method of claim 1, further comprising using said time-dependence for identifying transition between a capillary-porous colloidal state of the material and a colloidal-crystalline state of the material.

6. The method of claim 1, further comprising using said time-dependence for identifying transition between a discontinuous crystalline state of the material and a continuous crystalline state of the material.

7. The method of claim 1, further comprising using said time-dependence for determining a compressive strength of the material.

8. A system for determining setting period of a chemically-active material, comprising:
   a measuring unit, for continuously measuring an electrical property of the material to provide a time-dependence of said property, said property being a resistivity or a proxy thereof; and
   a processing unit, for defining, based on said time-dependence, a setting-start time and a setting-finish time, wherein said setting-start time is defined as a time of onset of a fastest rise of said resistivity and said setting-finish time is defined as a time of local maximum of said resistivity.

9. The system of claim 8, wherein said processing unit is configured for identifying transition between a workable state of the material and a non-workable state of the material, based on said time-dependence.

10. The method of claim 2, wherein said transition between said workable and said non-workable states is defined as a time of local minimum of said resistivity.

11. The method of claim 2, wherein said transition between said workable and said non-workable states is identified on a linear scale of said time-dependence.

12. The method of claim 10, wherein said local minimum is identified using a moving time window having a width of about 2 hours.

13. The system of claim 8, wherein said processing unit is configured for identifying transition between a first workable state of the material and a second workable state of the material, based on said time-dependence, said transition being equivalent to an abrupt slowing of slump that would have been observed had the material been subjected to a slump test.

14. The system of claim 8, wherein said transition between said first and said second workable states is defined as a time corresponding to a point of inflection of said resistivity.

15. The system of claim 8, wherein said transition between said first and said second workable states is identified on a linear scale of said time-dependence.

16. The system of claim 14, wherein said point of inflection is identified using a moving time window having a width of about 2 hours.

17. The system of claim 8, wherein said processing unit is configured for identifying transition between a gel state of the material and a capillary-porous colloidal state of the material, based on said time-dependence.

18. The system of claim 8, wherein said processing unit is configured for identifying transition between a capillary-porous colloidal state of the material and a colloidal-crystalline state of the material, based on said time-dependence.

19. The system of claim 8, wherein said processing unit is configured for identifying transition between a discontinuous crystalline state of the material and a continuous crystalline state of the material, based on said time-dependence.

20. The system of claim 8, wherein said processing unit is configured for determining a compressive strength of the material, based on said time-dependence.

21. The method of claim 1, wherein each of said setting-start and said setting-finish times is identified on a linear scale of said time-dependence.

22. The method of claim 1, wherein each of said onset of said fastest rise of said resistivity and said local maximum of said resistivity are identified using a moving time window having a width of about 2 hours.

23. The method of claim 1, wherein said electrical property is measured by direct contact with the material.

24. The method of claim 1, wherein said electrical property is measured in a constant volume.

25. The method of claim 1, wherein said electrical property is measured by generating an electric field between a first electrode and a second electrode along a sufficiently long contour within said material.

26. The method of claim 25, wherein said contour has a length which is at least two times the distance between said electrodes.

* * * * *